(12) United States Patent
Kim

(10) Patent No.: US 7,595,066 B2
(45) Date of Patent: Sep. 29, 2009

(54) COMPOSITION HAVING EFFECT OF MOXIBUSTION AND PRESS PELLET USING THE SAME

(76) Inventor: Jin Sub Kim, 410 Uldae-ri, Janghueng-myeon, Yangju-si, Gyeonggi-do 482-839 (KR)

( * ) Notice: Subject to any disclaimer, the term of this patent is extended or adjusted under 35 U.S.C. 154(b) by 0 days.

(21) Appl. No.: 11/628,275

(22) PCT Filed: Nov. 28, 2005

(86) PCT No.: PCT/KR2005/004022

§ 371 (c)(1),
(2), (4) Date: Nov. 29, 2006

(87) PCT Pub. No.: WO2006/059853

PCT Pub. Date: Jun. 8, 2006

(65) Prior Publication Data

US 2008/0063736 A1 Mar. 13, 2008

(30) Foreign Application Priority Data

Nov. 30, 2004 (KR) .................. 20-2004-0033932 U
Jul. 27, 2005 (KR) ...................... 10-2005-0068646

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS 5,592,956 A * 1/1997 Ju et al. ...................... 131/270

2002/0099322 A1 * 7/2002 Sakuta ........................ 604/20
2006/0030879 A1 * 2/2006 Spector ...................... 606/204

FOREIGN PATENT DOCUMENTS

| JP | 3242379 B2 | | 10/2001 |
|---|---|---|---|
| KR | 2001017617 | * | 3/2001 |
| KR | 0240389 Y1 | | 10/2001 |
| KR | 0293447 Y1 | | 10/2002 |
| KR | 0304241 Y1 | | 2/2003 |
| KR | 0292060 Y1 | | 10/2003 |
| KR | 2004-0022466 A | | 3/2004 |

OTHER PUBLICATIONS

How Stuff works, 2008, 3 pages, Artemisia, wormwood.*
Skye Flora, Mugwort, 2008, 3 pages.*
Plants for a future, 2008, 4 pages.*

* cited by examiner

*Primary Examiner*—Michael V Meller
(74) *Attorney, Agent, or Firm*—Daniel B. Schein, Esq.

(57) ABSTRACT

Disclosed herein is a composition with moxibustion effects comprising 20-40% by weight of an *artemisia* extract, 0-20% by weight of an auxiliary herbal material, 0-20% by weight of a resin and 30-60% by weight of a far-infrared radiating powder. Further disclosed is a method for preparing the composition, a press pellet for skin stimulation using the composition, and patch and sheet formulations comprising the composition. When the press pellet using the composition is attached to the affected parts or acupoints in a simple manner, acupuncture, moxibustion, far-infrared radiation and anion emission effects can be simultaneously attained.

6 Claims, 3 Drawing Sheets

COMPOSITION HAVING EFFECT OF MOXIBUSTION AND PRESS PELLET USING THE SAME

TECHNICAL FIELD

The present invention relates to a composition having moxibustion effects and a formulation acceptable in oriental medicine comprising the composition. More particularly, the present invention relates to a press pellet comprising a protrusion formed of or coated with a composition having moxibustion effects so as to exert both acupuncture and moxibustion effects.

BACKGROUND ART

Stimulation therapies, including acupuncture and moxibustion of meridian treatments, have been specifically established in oriental medicine through clinical tests for thousands of years, based on the fact that acupoints of meridians connected to the five viscera, the six internal organs, the head and the limbs are reaction and treatment points used for fighting against diseases. Extensive research has been conducted to treat and prevent diseases using acupoints. Under these circumstances, numerous stimulation devices and methods have been developed.

Representative examples of such stimulation methods are metal insertion methods and thermal methods using active ingredients of *artemisia*. That is, acupoint therapies are recognized as acupuncture-moxibustion treatments.

Moxibustion, which is a representative example of a variety of oriental medical treatments, refers to a method of treatment using heat released when *artemisia* is burnt.

In past years, moxibustion was performed by burning *artemisia* or a blend of *artemisia* and herbal materials. The benefits of moxibustion are not only dependent on the stimulation of the heat released when *artemisia* or herbal materials are burnt, but also on active ingredients of the *artemisia* and herbal materials. The active ingredients are absorbed into the skin of the affected parts and acupoints, achieving desired therapeutic effects.

However, there exist dangers of environmental pollution due to a lot of smoke released when *artemisia* is burnt. In addition, overheating may cause a burn and leave scars on the skin. For these reasons, people are unwilling to receive moxibustion despite its various benefits, which makes moxibustion difficult to popularize and globalize.

Since conventional thermal therapies were performed by burning *artemisia* or various herbal materials placed on the skin or acupoints, the risk of a burn was inevitable. In recent years, disposable indirect moxibustion and heating devices have been used in a simple manner without any risk of a burn. Further, moxibustion has been developed toward the utilization of chemical heat.

According to some advanced moxibustion techniques, moxibustion effects are achieved by preparing a lotion formulation containing extracts or active ingredients of *artemisia* and herbal materials without any thermal processing, applying the lotion formulation to the skin, and applying energy, e.g., electric heat, to the skin.

As the smoking effects of cigarettes are obtained when burnt, so the sedative effects of moxibustion are obtained due to heat released and chemical changes occurring in active ingredients of *artemisia* and herbal materials induced when burnt. In this point of view, the disadvantages of the techniques are that the full effects of active ingredients of *artemisia* are not attainable.

Further, smokeless moxibustion may be performed by using an additional heater.

However, this moxibustion has some disadvantages in that the procedure is troublesome and the effects are continued for a short period of time.

On the other hand, materials for acupuncture needles have been developed in the order of stones, bones and metals. Recently, a press pellet for inserting into the skin has been developed in the shape of a metal protrusion (FIG. 1). This press pellet doesn't inflict a wound on the skin and eliminates the risk of infection. The metal press pellet shown in FIG. 1 comprises an adhesive member 2, such as an adhesive plaster or tape, and an aluminum or copper protrusion 4 attached to the adhesive member 2. According to the press pellet, however, the skin is stimulated by the needle but moxibustion effects are unobtainable. Further, complex high-priced devices, e.g., electronic and laser needles, using a beam, electricity or magnetism have been developed, which are economically disadvantageous.

Thus, there is a strong need for a method or a device for simultaneously achieving both acupuncture and moxibustion effects in an easy and simple manner without an economic burden.

The present inventor has earnestly and intensively conducted research to overcome problems such as fear, detestation and inconvenience of patients against acupuncture and moxibustion. As a result, the present inventor has found that when functions of acupuncture for skin stimulation in acupoint therapies of oriental medicine are combined with those of moxibustion, the disadvantages of acupuncture (e.g., pain occurring from needle insertion and the danger of infection arising from organ damage caused by needle insertion) and the disadvantages of moxibustion (e.g., heat pain, burns, and smoke) are eliminated while creating complementary synergistic effects of acupuncture and moxibustion. The present invention has been achieved based on this finding.

DISCLOSURE OF THE INVENTION

In accordance with one aspect of the present invention, there is provided a composition with moxibustion effects comprising 20-40% by weight of a concentrated *artemisia* extract, 0-20% by weight of an auxiliary herbal material, 0-20% by weight of a resin, and 30-60% by weight of a far-infrared radiating powder.

In accordance with another aspect of the present invention, there is provided a method for preparing a composition with moxibustion effects, the method comprising the steps of:

cutting or pulverizing *artemisia*, mixing the cut or pulverized *artemisia* with rice vinegar in a volume of 1.5 liters per 10 kg of the cut or pulverized *artemisia*, separately processing the mixture in each pot using controlled heat through each mild firing, medium firing and strong firing, extracting the processed mixture with boiling water in an amount of about 7-10 times that of the *artemisia*, and concentrating the extract until the weight ratio of active ingredients of the *artemisia* to the water becomes 5-7:3-5;

processing an auxiliary herbal material to prepare a decoction and concentrating the decoction until the content of active ingredients of the auxiliary herbal material becomes 20-30% by weight of the decoction;

dissolving a resin in a 70% alcohol, purifying the alcoholic solution by precipitation to obtain a resin tincture in which the weight ratio of the alcohol to active ingredients of the resin is 5-9:1-5, and adding the resin tincture to honey diluted with distilled water, comprising 30-50% by weight of honey to make the resin water-soluble, the resin tincture being added in the same volume as that of the dilution; and mixing the *artemisia* extract, the auxiliary herbal material extract and the water-soluble resin prepared in the previous steps, followed by mixing with a far-infrared radiating powder.

In accordance with another aspect of the present invention, there is provided a press pellet for skin stimulation which comprises a protrusion formed of or coated with at least one material selected from the group consisting of active ingredients of *artemisia*, herbal materials acceptable in oriental medicine, resins acceptable in oriental medicine and far-infrared radiating powders, and an adhesive member attached to the bottom of the protrusion.

In accordance with yet another aspect of the present invention, there is provided a patch or sheet formulation comprising the composition.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
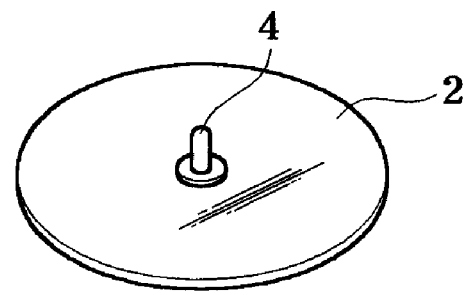
FIG. 1 is a view showing the structure of a conventional metal press pellet.
Figure 2:
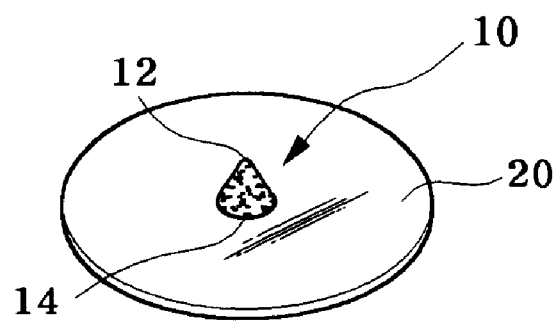
FIGS. 2 to 6 are views showing various shapes of press pellets for skin stimulation according to embodiments of the present invention.
Figure 3:
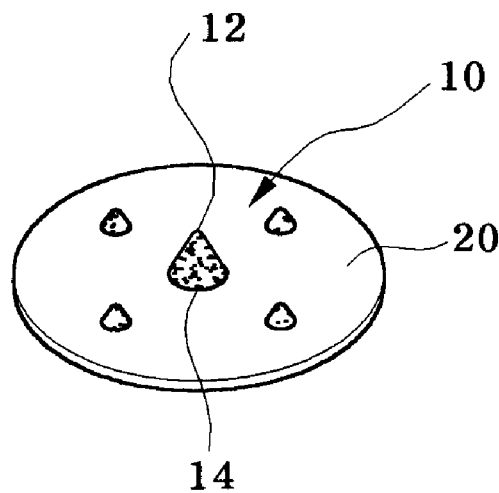
Figure 4:
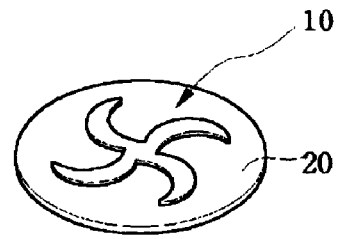
Figure 5:
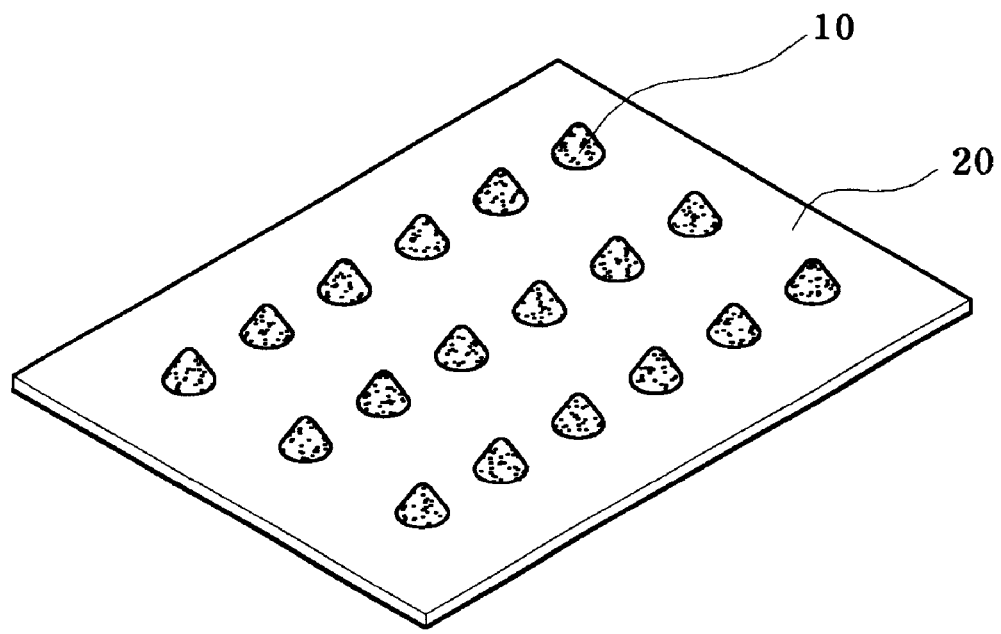
Figure 6:
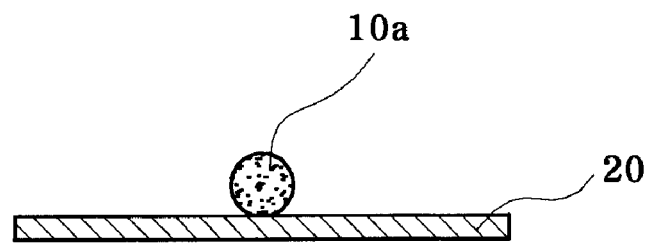

Hereinafter, the present invention will be described in more detail.

The present invention provides a composition with moxibustion effects comprising 20-40% by weight of an *artemisia* extract, 0-20% by weight of an auxiliary herbal material, 0-20% by weight of a resin, and 30-60% by weight of a far-infrared radiating powder.

The present invention also provides a method for preparing a composition with moxibustion effects which comprises the steps of:

cutting or pulverizing *artemisia*, mixing the cut or pulverized *artemisia* with rice vinegar in a volume of 1.5 liters per 10 kg of the cut or pulverized *artemisia*, separately processing the mixture in each pot using controlled heat through each mild firing, medium firing and strong firing, extracting the processed mixture with boiling water in an amount of about 7-10 times that of the *artemisia*, and concentrating the extract until the weight ratio of active ingredients of the *artemisia* to the water becomes 5-7:3-5;

processing an auxiliary herbal material to prepare a decoction and concentrating the decoction until the content of active ingredients of the auxiliary herbal material becomes 20-30% by weight of the decoction;

dissolving a resin in a 70% alcohol, purifying the alcoholic solution by precipitation to obtain a resin tincture in which the weight ratio of the alcohol to active ingredients of the resin is 5-9:1-5, and adding the resin tincture to honey diluted with distilled water, comprising 30-50% by weight of honey to make the resin water-soluble, the resin tincture being added in the same volume as that of the dilution; and mixing the *artemisia* extract, the auxiliary herbal material extract and the water-soluble resin prepared in the previous steps, followed by mixing with a far-infrared radiating powder.

Examples of the concentrated *artemisia* extract used in the present invention include, but are not limited to, *Artemisia argyi* Lev et Vant and *Artemisia asiatica* Nakai. *Artemisia* species growing naturally in Korea are preferred, and particularly, *Artemisia* spp. is more preferred.

To attain unchanged moxibustion effects, it is preferred that the concentrated *artemisia* extract includes a blackish *artemisia* extract, a yellowish *artemisia* extract and a brownish *artemisia* extract, all of which are prepared by stir-baking in accordance with the drug processing prescribed in oriental medicine.

The concentrated *artemisia* extract is prepared in accordance with the following procedure. First, *artemisia* is cut or pulverized. The cut or pulverized *artemisia* is mixed with rice vinegar in a volume of 1.5 liters per 10 kg of the cut or pulverized *artemisia*, and then the mixture is separately processed in each pot using controlled heat through each mild firing, medium firing, strong firing, and the like. Thereafter, the processed mixture is extracted with boiling water in an amount of about 7-10 times that of the *artemisia*. The resulting mixture is concentrated by heating so that the content of active ingredients of the *artemisia* is from about 7% to about 8%, and the water content is from about 25% to about 50% and preferably 30% on a dry weight basis. Since the concentrated *artemisia* extract thus obtained is a highly viscous paste, the use of an additional adhesive is avoided.

The auxiliary herbal material used in the composition of the present invention is preferably at least one kind selected from the group consisting of *Angelicae Dahuricae Radix*, *Clematidis Radix* and *Cnidii Rhizoma*. The auxiliary herbal material, such as *Angelicae Dahuricae Radix*, *Clematidis Radix* or *Cnidii Rhizoma*, is processed to prepare a decoction, and the decoction is purified and concentrated until the content of active ingredients of the auxiliary herbal material becomes 20-30% by weight of the decoction.

The auxiliary herbal material, such as *Angelicae Dahuricae Radix*, *Clematidis Radix* or *Cnidii Rhizoma*, used in the composition of the present invention may exert a synergistic effect with the *artemisia* extract, thus providing beneficial effects, including improvement in blood circulation, sedation, alleviation of pain, treatment of neuralgia, bruise and arthritis, and skin regeneration.

The resin used in the composition of the present invention is preferably at least one material selected from the group consisting of olibanum, rosin, myrrha, borneol, camphor, menthol and capsicum tincture, but is not particularly limited thereto.

Since olibanum and myrrha as the resin ingredients have poor water solubility, they are difficult to be absorbed into skin when used for external applications. For enhanced absorptiveness and improved effects, each of the resin ingredients is dissolved in a 70% alcohol and purified by precipitation to obtain a 5-50% resin tincture, preferably, a 10% resin tincture. Then, the resin tincture is added to honey diluted with distilled water, comprising 30-50% by weight of honey to make the resin water-soluble. At this time, the resin tincture is added in the same volume as that of the dilution used. The resin contained in the composition of the present invention serves to activate cell functions, such as promotion of the Gi (vital energy) and blood flow, anti-inflammation, alleviation of pain and skin regeneration, and to increase the number of leukocytes, resulting in immune enhancement. In the case of a 10% resin tincture having a relatively high alcohol content, the alcohol is vaporized during subsequent production of a press pellet, leading to rapid drying of the press pellet.

The kind of the far-infrared radiating powder used in the composition of the present invention is not particularly limited so long as far-infrared rays can be radiated. Far-infrared radiating powders capable of exhibiting anion emission effects are particularly preferred. As the far-infrared radiating powder used in the present invention, at least one mineral selected from the group consisting of bioceramics, tourmaline, kiyoseki, quartz porphyry, illite, biotite, germanium and monazite is preferably used.

The bioceramic or mineral such as kiyoseki, is preferably pulverized into nanomolecules having a size of 1,000 mesh or more. This increase in the surface area of the bioceramic or mineral is preferred in terms of moxibustion, far-infrared radiation and anion emission effects.

A large quantity of energy, such as far-infrared rays and anions, are released at body temperature due to vigorous molecular motions of the ultra fine mineral or bioceramic powder of the order of microns, which is close to the size of nanomolecules. The released energy replaces heat required to burn *artemisia* and thus functions beneficial to humans can be attained.

Further, since the far-infrared radiating powder used in the composition of the present invention is pulverized into nanomolecules having a size of 1,000 mesh or more, it has a maximized surface area. When a mixture of the highly viscous concentrated *artemisia* extract, the *Clematidis Radix* solution, the water-soluble olibanum resin is dripped in the state of a highly viscous gel using a quantitative discharger to form spherical or conical protrusions of a press pellet, the far-infrared radiating powder weakens the surface tension and thus the contained alcohol is rapidly vaporized along with the water without compressive deformation when drying. Accordingly, the use of the far-infrared radiating powder in the composition of the present invention increases the productivity of the final press pellet and provides the desired moxibustion and acupuncture effects without heating.

The present invention also provides a press pellet for skin stimulation which comprises a protrusion formed of or coated with at least one material selected from the group consisting of active ingredients of *artemisia*, herbal materials acceptable in oriental medicine, resins acceptable in oriental medicine and far-infrared radiating powders, and an adhesive member attached to the bottom of the protrusion.

The protrusion is not specially limited so long as it is formed of or coated with the at least one material. It is particularly preferred that the protrusion be formed of or coated with the composition having moxibustion effects according to the present invention.

The protrusion of the press pellet for skin stimulation may be formed of a composition containing active ingredients of *artemisia*. Alternatively, the protrusion may be formed by coating a press pellet member made of a material acceptable in oriental medicine, for example, aluminum or copper, with a composition containing active ingredients of *artemisia*. It is preferred that the protrusion be formed in the shape of a cone, push pin, hemisphere, or sphere.

As shown in FIGS. 2 to 6, one or more protrusions of the press pellet for skin stimulation are attached on the surface of an adhesive member. The protrusions may be formed in various shapes, e.g., one-point, three-point, multi-point, wave, tauguk and diamond.

Suitable adhesives for the adhesive member include general adhesives that can be used in sheet and patch formulations. It is more preferred to mix a portion or all of the composition with the adhesive to form the adhesive member. It is preferred to apply the composition to the skin as broadly as possible in order to achieve the desired effects. To this end, the composition is concentrated into a highly viscous gel having a solvent content of 30% or less, or is dried and pulverized into a powder. Thereafter, the adhesive is mixed with 0.5~1 part by weight of the gel or powder relative to 100 parts by weight of the total adhesive. In doing so, the effects of the press pellet and the active ingredients contained in the adhesive can be doubled.

As shown in FIGS. 2 to 6, the press pellet for skin stimulation according to the present invention is produced by simultaneously and quantitatively discharging the mixture in the shape of a one-point, three-point or multi-point, which has a weight of 2-5 mg, a diameter of 1-2 mm and a height of 1-1.5 mm, on the surface of the adhesive member, which is previously processed to have a proper size.

Figure 7:
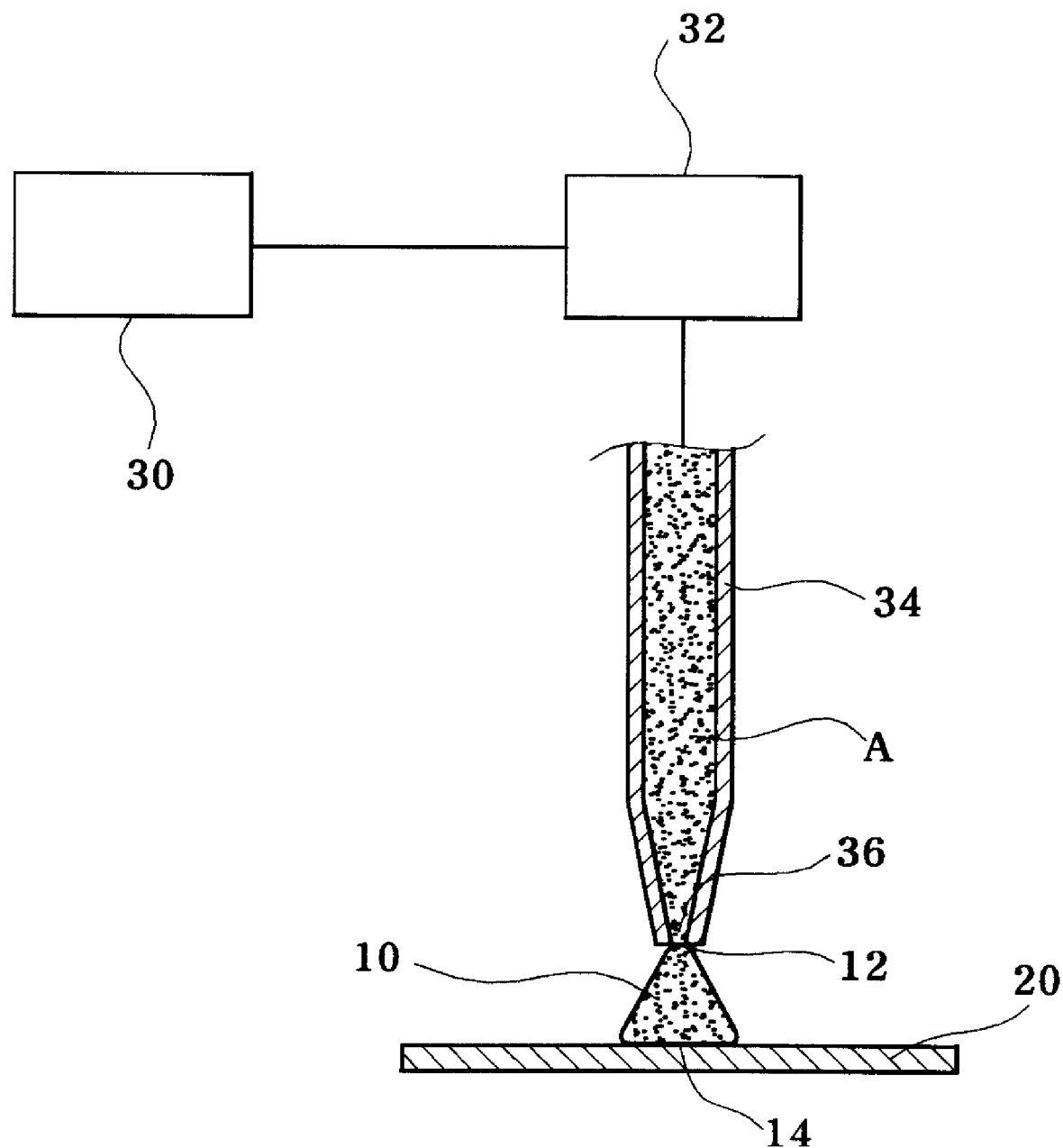
FIG. 7 is a view showing a state wherein a press pellet for skin stimulation according to the present invention is produced by injection molding using a quantitative discharger.

FIG. 7 is a view showing a state wherein the press pellet for skin stimulation according to the present invention is produced by injection molding using a quantitative discharger. As shown in FIG. 7, first, the composition (A) is transferred from a drug raw material supply part 30 to a drug raw material supply unit 32. The composition (A) is supplied from the drug raw material supply unit 32 to a spray nozzle 34. The composition (A) is discharged from the spray nozzle 34 through a discharge port 36 to form a protrusion 10 on an adhesive member 20. Immediately after the composition (A) is discharged on the adhesive member 20, the protrusion 10 is adhered to the adhesive member 20, completing production of the press pellet according to the present invention.

Alternatively, the press pellet for skin stimulation according to the present invention may be produced in accordance with the following procedure. First, the herbal material solution is concentrated. The concentrate is mixed with the mineral powder until the solvent content becomes 10% or less, and then the mixture is formed into a press pellet or granular pill and dried. Thereafter, the dried pellet or pill is attached on the surface of the adhesive member to produce the final press pellet. Or, a solvent is added to dilute the mixture to a proper concentration, applied to a press pellet member made of a metal or a synthetic resin, and dried to produce the final press pellet.

When the press pellet for skin stimulation according to the present invention is used, the composition having moxibustion effects is dissolved in moisture discharged from the skin with the passage of time, and absorbed into the skin through extended skin pores by the pressurization of the press pellet by osmotic pressure, thus attaining the desired effects.

Specifically, when the press pellet of the present invention is attached to the skin, the skin membrane is stretched by 50% or more, which broadens the size of skin pores, and subcutaneous tissues are pressurized, causing physical changes in the subcutaneous tissues by the stimulation of the needle. Thereafter, moisture discharged from the skin is well absorbed by the press pellet in which moisture is sealed. Since active ingredients of the herbal material are dissolved and rapidly absorbed through the stretched skin membrane by osmotic pressure, the press pellet of the present invention exerts not only superior acupuncture effects but also a synergistic effect of moxibustion, far-infrared radiation and anion emission effects without heating.

The present invention also provides a patch or sheet formulation comprising a composition having moxibustion effects prepared by the method. The patch and sheet formulations can be produced in accordance with general procedures known in the art.

The present invention will now be described in more detail with reference to the following preferred examples. However, these examples are given for the purpose of illustration and are not to be construed as limiting the scope of the invention.

EXAMPLES

Example 1

Preparation of Composition with Moxibustion Effects and Production of Press Pellet for Skin Stimulation 38% by weight of an concentrated *artemisia* extract, 6% by weight of a *Clematidis Radix* extract, 18% by weight of an olibanum tincture, and 38% by weight of a kiyoseki powder were mixed to prepare a composition having moxibustion effects.

The composition 1.5 mg (solvent content: ~30%) was discharged through a discharge port (Φ=2 mm) of a quantitative discharger so as to be in contact with the surface of an adhesive tape as an adhesive member to form a spherical protrusion with a diameter of 2 mm and a height of about 1.2 mm, completing production of a press pellet. The shape of the press pellet was maintained even after being dried. The press pellet is suitable to use where the skin is sensitive and for use in children.

Example 2

Preparation of Composition with Moxibustion Effects and Production of Press Pellet for Skin Stimulation 38% by weight of an concentrated *artemisia* extract, 5% by weight of a *Cnidii Rhizoma* extract, 13% by weight of an olibanum tincture, 1% by weight of borneol, 1% by weight of camphor (or menthol), 1% by weight of a capsicum tincture, and 41% by weight of a bioceramic powder were mixed to prepare a composition having moxibustion effects.

The composition (solvent content: ~25%) was discharged through a discharge port (Φ=2 mm) of a quantitative discharger so as to be in contact with the surface of an adhesive tape as an adhesive member while the discharge port was slowly raised upward to form a conical needle-shaped protrusion with a weight of about 1.5 mg, a diameter of about 2 mm and a height of about 1.5-1.7 mm, completing production of a press pellet. Immediately after the discharge, the press pellet was dried in a heating/drying system at about 60° C. for 3 minutes, and packaged. The product containing menthol, a capsicum tincture and the like has high stimulation and penetration power. Accordingly, the press pellet is highly stimulative, which is thus effective in using where the skin is insensitive and for use in adults.

Example 3

Production of Press Pellet

30% by weight of an concentrated *artemisia* extract (moisture content: 50%), 7% by weight of an *Angelicae Dahuricae Radix* extract, 3% by weight of a *Clematidis Radix* extract, 10% by weight of an olibanum or myrrha extract, 25% by weight of a bioceramic powder, and 25% by weight of a natural mineral powder were mixed to prepare a highly viscous concentrate containing the plant ingredients. The concentrate was discharged using a quantitative discharger on the surface of an adhesive tape as an adhesive member to produce a press pellet, and then dried.

Experimental Example 1

Clinical Tests 96 of 102 clinical cases who had been treated with the press pellet for skin stimulation, which was produced in Example 3, during the period of Dec. 1, 2004 to Apr. 30, 2005, were selected. Results were determined on the selected cases.

The patients included 38 males and 58 females. Nine of the patients were aged in their twenties; twenty-one were aged in their thirties; forty five were aged in their forties; eight were aged in their fifties; and thirteen were aged in their sixty or over. The patients' occupations included forty one housewives, eighteen public servants, twelve drivers, ten office workers, eight jobless men, and the like.

The affected parts or acupoints of the patients were washed using sterilized cotton, and then the press pellet was attached thereto. When the area of the affected parts or acupoints was small, one press pellet was used. Meanwhile, when the area of the affected parts or acupoints was large, three to five press pellets, as needed, were further attached at a distance of 3 cm or more apart from the affected parts or acupoints. If an itching sensation was felt, the press pellet was removed. The press pellet was allowed to stand for two or more days until it was finally detached. Thereafter, residues on the affected parts or acupoints were washed off and then the press pellet was again attached.

The experimental results are shown in Table 1.

TABLE 1

| Disease | Number of cases | Disappearance of symptoms | Improvement of symptoms | Unknown |
| --- | --- | --- | --- | --- |
| Podalgia | 8 | 5 | 2 | 1 |
| Sciatica | 13 | 8 | 1 | 4 |
| Arthralgia | 26 | 19 | 5 | 2 |
| Lumbago due to strain and contusion | 11 | 8 | 1 | 2 |
| Gastritis | 10 | 5 | 3 | 2 |
| Hypertension | 7 | 1 | 3 | 3 |
| Neurasthenia | 13 | 8 | 2 | 3 |
| Menorrhalgia | 6 | 5 | 1 | 1 |
| Growing pain | 2 | 1 | — | 1 |

Experimental Example 2

A 36 year old female bank clerk who had suffered from upper abdominal dropsy and pain, nausea, lumbago, indigestion and the like was diagnosed as having gastroptosis by X-ray fluoroscopy. The press pellets produced in Example 3 were attached on Yangmun (ST 21 acupoint), Cheonchu (ST 25 acupoint) and Gihae (CC 6 acupoint) every three days. The gastroptosis was completely treated after one month following the attachment.

Experimental Example 3

A first-aid treatment was given to a 45 year old male guard who had his waist dislocated while transporting a heavy object was presumably suffering from acute lumbar sprain, and could not stretch and bend his body forward or backward. Thereafter, the press pellets produced in Example 3 were attached on Asihyeol (acupoint selected by eliciting tenderness or pain at the site of sensitivity) and its adjacent tender nerve points. Pain was alleviated after two days, and completely disappeared after three days following the attachment.

Experimental Example 4

A 36 year old male public servant who had been afflicted with dizziness, headache, insomnia, amnesia, sexual neurasthenia, and the like for past 4 years was diagnosed as having a nervous breakdown. The press pellets produced in Example 3 were attached on Johae (KI 6 acupoint). Singwol (CC 8 acupoint) Sinmun (HT 7 acupoint), and the like. The patient was observed for three months while new press pellets were changed every three days. As a result, all symptoms other than dizziness and sexual nervous breakdown were improved.

Experimental Example 5

The press pellets produced in Example 3 were attached on Naegwan (PC 6 acupoint), Simsu (BL 15 acupoint), Gyeoksu (BL 17 acupoint) and Baekoe (GC 20 acupoint) of a 55 year old male mechanic who had suffered from hypertension (blood pressure: 180/100 mmHg). The blood pressure dropped to 130/92 mmHg after three days, and further dropped to 120~130/80~88 mmHg after one month following the attachment.

Experimental Example 6

A 17 year old male student who had suffered from arthralgia of extremities due to fever (body temperature: 38.4° C.), headaches, nasal obstruction, burning throat, rigor, was diagnosed as having influenza. The press pellets produced in Example 3 were attached on Daechu (GC 14 acupoint), Eoje (LU 10 acupoint), Pungbu (GC 16 acupoint), and Pyesu (BL 13 acupoint). After one day following the attachment, the body temperature became normal and the other symptoms disappeared.

Experimental Example 7

The press pellets produced in Example 3 were attached on Junggeuk (CC 3 acupoint), Gwanwon (CC 4 acupoint), and Busa (SP 13 acupoint) and Yudo (GB 28 acupoint) of the lower abdominal muscle of a 28 year old female graduate student who had suffered from menorrhalgia. New press pellets were changed every other day throughout the menstrual period. As a result, the menstrual pains were substantially gone after two months following the attachment.

Experimental Example 8

A 14 year old male student who had suffered from enuresis from his primary school days had normal growth and nutrition, but was skinny. He had myoglobinuria due to a lower abdominal cold and felt heavy in the abdominal region when urination. The press pellets produced in Example 3 were attached on Subun (CC 9 acupoint), Gwanwon (CC 4 acupoint), Junggeuk (CC 3 acupoint) and left and right points of the lower abdominal muscle. The symptoms were almost treated after two weeks following the attachment.

Experimental Example 9

A 51 year old housewife who had suffered from painful temples (Taeyang (EX-HN 5 extra point)) at both sides of the eyes, a sick headache on the left head, a high blood pressure of 130/85 mmHg, constipation, fatigue and insomnia was diagnosed as having migraine. After the press pellets produced in Example 3 were attached on Jogimeup (GB 41 acupoint), Hyeopgye (GB 43 acupoint), and points of the lower stemocleidomastoid muscle, he was allowed to fall asleep and prohibited from overwork. The symptoms were improved after five days following the attachment.

Experimental Example 10

The bloodletting was carried out through Hyeopcheok (EX-B 2 extra point) of a 56 year old female patient, who could not lift her arms high due to right adhesive capsulitis, had benumbed hands, and had pains in the sides of the exterior of elbow so that she could not have fall asleep. Thereafter, the press pellets produced in Example 3 were attached on her brachioradialis. The adhesive capsulitis was substantially treated after one week after the attachment.

INDUSTRIAL APPLICABILITY

As apparent from the above description, according to the composition of the present invention, a blend of *artemisia*, an auxiliary herbal material and a resin can be penetrated into the skin to obtain moxibustion effects. In addition, since the composition of the present invention comprises a bioceramic or a mineral powder, the benefits of *artemisia* can be further utilized without the need for an additional heater and far-infrared radiation and anion emission effects can be attained. Furthermore, since the press pellet for skin stimulation according to the present invention has a spherical or conical shape, acupoints on the skin can be can pressurized and stimulated, thus achieving acupuncture effects.

In conclusion, when the press pellet for skin stimulation according to the present invention is attached to the affected parts or acupoints in an easy and simple manner by everyone, a variety of effects, including acupuncture, moxibustion, far-infrared radiation and anion emission effects, can be simultaneously attained.

The invention claimed is:

1. A press pellet for skin stimulation, comprising a protrusion formed of or coated with a composition with moxibustion effects, said composition comprising:
   20-40% by weight of a concentrated *artemisia* extract;
   an auxiliary herbal material;
   a water-soluble tincture;
   30-60% by weight of a far-infrared radiating powder; and
   an adhesive member attached to the bottom of the protrusion;
   wherein the concentrated *artemisia* extract is manufactured by i) heating a mixture of *artemisia* and rice vinegar; ii) extracting the mixture of *artemisia* and rice vinegar with boiling water; and iii) concentrating the extract, and
   wherein the water-soluble tincture is obtained from ingredients comprising at least one of the group consisting of olibanum, rosin, myrrha, borneol, camphor and capsicum.

2. The press pellet according to claim 1, wherein the protrusion is formed in the shape of a cone, push pin, hemisphere, or sphere.

3. The press pellet according to claim 1, wherein one or more protrusions attached on the surface of the adhesive member are formed in a one-point, three-point, multi-point, wave, tauguk, or diamond shape.

4. The press pellet according to claim 1, wherein an adhesive contained in the adhesive member comprises a portion or all of said composition with moxibustion effects.

5. The press pellet of claim 1, wherein said far-infrared radiating powder comprises quartz porphyry.

6. The press pellet of claim 1, wherein said auxiliary herbal material comprises *Cnidii Rhizoma*.

* * * * *